US006669476B2

(12) United States Patent
Prestipino et al.

(10) Patent No.: US 6,669,476 B2
(45) Date of Patent: Dec. 30, 2003

(54) NANOPHASE DENTAL PROSTHETICS AND METHOD

(76) Inventors: David Michael Prestipino, 521 Bushy Ridge Dr., Star Tannery, VA (US) 22654; Vincent Joseph Prestipino, 14633 Crossway Rd., Rockville, MD (US) 20853

( * ) Notice: Subject to any disclaimer, the term of this patent is extended or adjusted under 35 U.S.C. 154(b) by 35 days.

(21) Appl. No.: 09/983,162

(22) Filed: Oct. 25, 2001

(65) Prior Publication Data

US 2002/0028424 A1 Mar. 7, 2002

Related U.S. Application Data

(63) Continuation-in-part of application No. 09/604,413, filed on Jun. 27, 2000, now abandoned.

(51) Int. Cl.[7] .............................................. A61C 13/00
(52) U.S. Cl. ................................. 433/201.1; 433/167
(58) Field of Search .................... 433/167, 172, 433/173, 201.1, 202.1

(56) References Cited

U.S. PATENT DOCUMENTS

| 4,737,411 A | 4/1988 | Graves, Jr. et al. |
| 5,125,839 A | 6/1992 | Ingber et al. |
| 5,223,186 A | 6/1993 | Eastman et al. |
| 5,417,956 A | 5/1995 | Moser |
| 5,571,016 A | 11/1996 | Ingber et al. |
| 5,772,439 A | 6/1998 | Yamaoka et al. |
| 5,989,026 A | 11/1999 | Rogers et al. |
| 6,013,591 A | 1/2000 | Ying et al. |
| 6,270,347 B1 * | 8/2001 | Webster et al. ............. 433/173 |

FOREIGN PATENT DOCUMENTS

| EP | 0 438 048 A1 | 7/1991 |
| WO | WO 91/08713 | 6/1991 |

OTHER PUBLICATIONS

Siegel, Richard W., Creating Nanophase Materials, Scientific American, Dec. 1996, pp. 74–79.

* cited by examiner

*Primary Examiner*—Kevin Shaver
*Assistant Examiner*—Melba Bumgarner
(74) *Attorney, Agent, or Firm*—Stephen Christopher Swift; Swift Law Office

(57) ABSTRACT

Dental prosthetics, including implants, crowns and bridges, made from nanophase materials. The nanophase materials are generally manufactured by evaporating a metal or other solid substrate by heating it to a temperature at or above its boiling point in a vacuum to form a vapor. The vapor is then condensed back to a solid state through contact with a cold gas. In a first method, the nanophase material is heated until it is in a fluid state, then it is poured into a mold and cooled to form all or part of a dental prosthetic. In a second method, the nanophase material is placed into the mold in a powdered form, then heated so that the grains form a solid mass. Nanophase crowns and bridges should generally be formed in one piece, but the upper surface of a nanophase prosthetic will usually be covered with porcelain or another non-nanophase material.

12 Claims, 7 Drawing Sheets

NANOPHASE DENTAL PROSTHETICS AND METHOD

CROSS REFERENCE TO RELATED APPLICATION

This application is a Continuation-in-part of Utility patent application Ser. No. 09/604,413, filed Jun. 27, 2000 now abandoned.

BACKGROUND OF THE INVENTION

1. Field of the Invention

The present invention relates to dental prosthetics, including implants, crowns and bridges made using materials formed by nanophase technology.

2. Description of the Prior Art

Dental prosthetics may be used to replace all or a portion of one or more natural teeth. A dental implant is a portion of a dental prosthetic that is anchored in the jawbone, and is used when an entire tooth has been lost. Dental crowns replace the top part of a natural tooth that has been badly decayed or otherwise damaged. Bridges are two or more crowns on adjacent teeth that are joined together in one piece for extra strength. Dental implants, crowns and bridges are collectively referred to as "dental prosthetics" or "restoratives." With all dental prosthetics it is desirable to have a hard material that is unlikely to break. Nanophase materials, which may be ceramic or metallic, are a new kind of material that is much harder than conventional materials. While nanophase materials are disclosed in the prior art, the use of nanophase materials in dental prosthetics is not disclosed in the prior art. (For a brief general introduction to the subject of nanophase materials, see Siegel, Richard W., Creating Nanophase Materials, Scientific American, December 1996, pp. 74–79.)

U.S. Pat. No. 4,737,411, issued on Apr. 12, 1988, to George A. Graves, Jr., Dale E. McCullum and Steven M. Goodrich, discloses controlled pore size ceramics designed for dental and orthopaedic applications. The ceramic composite has an open porous network of controlled pore size comprising ceramic particles fused by a coating of glass on their surfaces. The instant invention is distinguishable, in that it uses nanophase technology, and does not require a glass coating to bind particles.

U.S. Pat. No. 5,125,839, issued on Jun. 30, 1992, to Abraham Ingber, Vincent Prestipino and Anopet Phimmasone, discloses a bone-embedded implant fixture interfaced with an aluminum oxide abutment post. The instant invention is distinguishable, in that it uses materials formed by nanophase technology.

U.S. Pat. No. 5,223,186, issued on Jun. 29, 1993, to Jeffrey A. Eastman, Kurt E. Sickafus and Joel D. Katz, discloses microwave sintering of nanophase ceramics without concomitant grain growth. The instant invention is distinguishable, in that it makes use of nanophase materials in dental prosthetics.

U.S. Pat. No. 5,417,956, issued on May 23, 1995, to William R. Moser, discloses a process for the preparation of nanophase solid state materials, and novel materials formed by the process. The instant invention is distinguishable, in that it makes use of nanophase materials in dental prosthetics.

U.S. Pat. No. 5,571,016, issued on Nov. 5, 1996, to Abraham Ingber, Vincent Prestipino and Anopet Phimmasone, discloses a dental implant system, interfaced with a ceramic abutment post. The instant invention is distinguishable, in that it uses materials formed by nanophase technology.

U.S. Pat. No. 5,772,439, issued on Jun. 30, 1998, to Akira Yamaoka et al., discloses a hybrid dental implant, having cementum particles on the surface of a substrate, but does not disclose the use of nanophase materials.

U.S. Pat. No. 5,989,026, issued on Nov. 23, 1999, to Dan Paul Rogers, Gale R. Brown and Daniel Y. Sullivan, discloses a ceramic two-piece dental abutment, but does not disclose the use of nanophase materials in making the abutment.

U.S. Pat. No. 6,013,591, issued on Jan. 11, 2000, to Jackie Y. Ying, Edward S. Ahn and Atsushi Nakahira, briefly mentions the use of "bioceramics", i.e., biologically compatible ceramics, "in peridontic and orthopedic applications as well as oral, plastic, and ear, nose, and throat surgery." (Column 1, lines 58–60.) It also discloses that use of a "nanocrystalline apatite article" as a "prostheis". (Column 11, lines 34–40.) It does not disclose dental prosthetics made from a combination of ceramic and metallic nanophase materials, nor the use of molds to form dental prosthetics from nanophase materials, as in the instant invention. It also does not disclose dental prosthetics made of biologically inert nanophase materials.

International Patent Application No. 91/08713, filed pursuant to the Patent Cooperation Treaty, published on Jun. 27, 1991, inventor Volkhard-Hagen Clostermann, discloses a threaded body for securing a multi-part tooth replacement, but does not disclose the use of nanophase materials.

European Patent Application No. 438 048 A1, published on Jul. 24, 1991, inventor Dr. Prof. Willi Schulte, discloses a dental implant with jaw anchored posts, but does not disclose the use of nanophase materials.

It can be seen that none of the above prior art patents disclose the use of nanophase materials in dental implants, crowns or bridges. None of the above inventions and patents, taken either singly or in combination, is seen to describe the instant invention as claimed.

SUMMARY OF THE INVENTION

The invention is the use of materials prepared by nanophase technology in dental prosthetics. Nanophase materials are formed by heating and evaporating an ordinary metal or other solid material in a vacuum, and then condensing it back to the solid state using a cold gas, so that the atoms or molecules of the materials form very small clusters. The fact that the atomic or molecular clusters are very small gives nanophase materials unusual properties, including great strength or hardness. Dental implants are inserted into the bone in a patient's jaw, and are used with prosthetics to replace lost teeth that commonly have both metallic and ceramic portions. Dental implants made from nanophase materials have the advantage of increased hardness over conventional materials, which makes them less likely to break. Nanophase materials may also be used in dental crowns and bridges. Accordingly, it is a principal object of the invention to provide improved dental implants.

It is another object of the invention to provide improved dental crowns and bridges.

It is a further object of the invention to provide improved ceramic parts of dental prosthetics.

Still another object of the invention is to provide improved metallic dental prosthetics.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is the use of materials prepared by nanophase technology in dental prosthetics.

Figure 1:
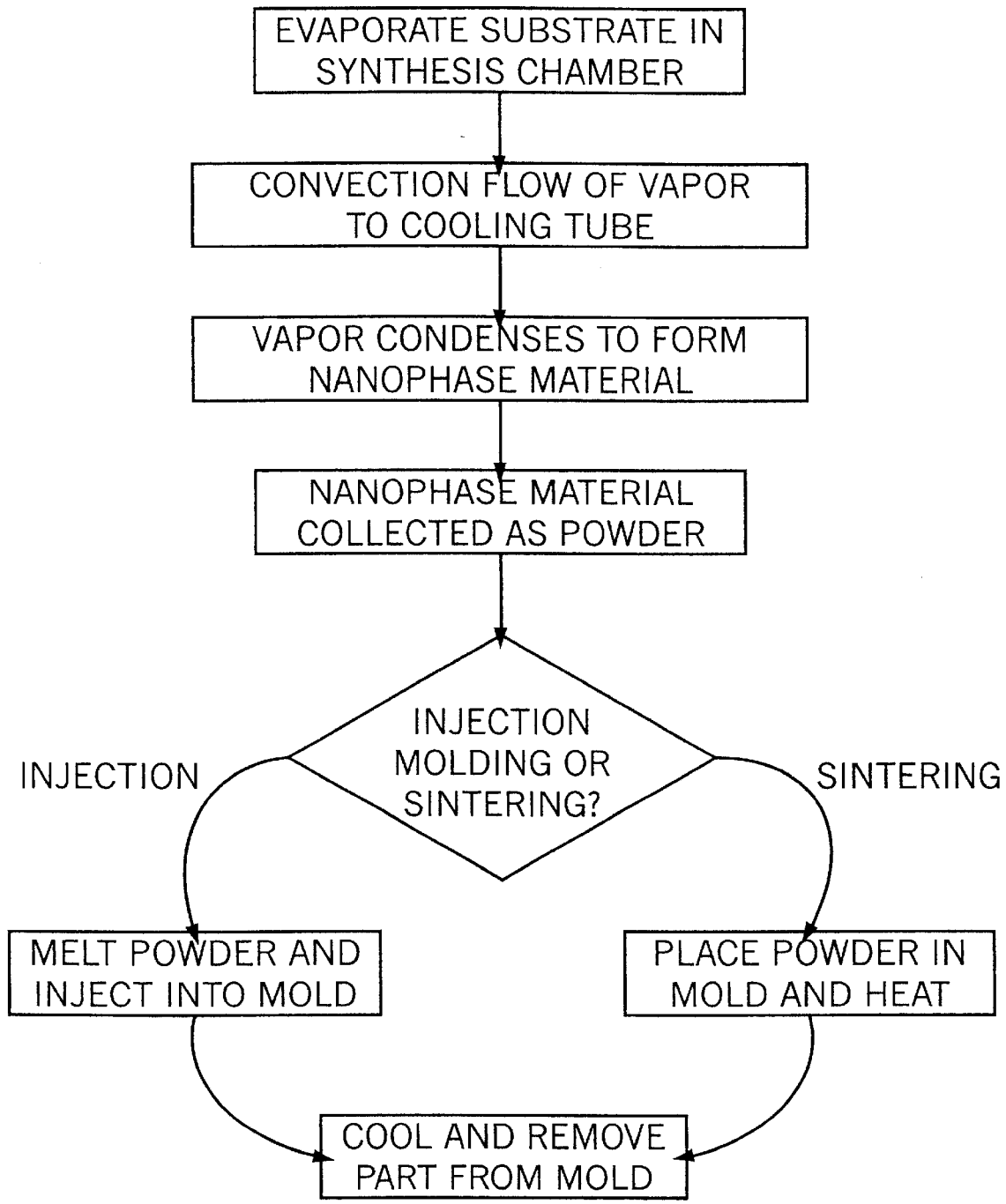
FIG. 1 is a flow chart showing the process typically used in forming nanophase metals.

FIG. 1 is a flow chart showing the process typically used in forming nanophase metals. A metal or other substrate of conventional material is heated in a vacuum in a synthesis chamber to a temperature at or above its boiling point. This causes atoms (or molecules) to evaporate from the surface of the substrate. Gas convection flow causes the vapor thus formed to move from the synthesis chamber through a conduit to a cooling tube. The cooling tube may be surrounded by a refrigerant such as liquid nitrogen. If a metallic nanophase product is desired, the cooling tube may be filled by an inert gas such as helium, which will absorb heat from the vapor without reacting with it. If a ceramic nanophase product is desired, the cooling tube may be filled with a reactive gas such as oxygen, or a mixture of inert and reactive gases. In either case, under controlled conditions of temperature and pressure, contact with the cold gas will cause the atoms or molecules of the vapor to condense into very small clusters (or "grains"). These very small atomic or molecular clusters are what constitute the difference between nanophase and conventional materials. Grains in conventional materials range from microns to millimeters in diameter, with each grain containing several billion atoms. Grains in nanophase materials are generally less than one hundred nanometers in diameter, and contain fewer than tens of thousands of atoms. Because of the small size of their grains, nanophase materials have several unusual physical properties, including much greater strength because of the absence of significant dislocations between the grains.

The nanophase grains form a powder in the cooling tube, which is then collected. A part of a dental prosthetic may then be formed from the powder, either by injection molding, or by sintering. In injection molding, the powder is heated until it melts, and then is injected into a mold. Alternatively, the powder may be placed in the mold, and then heated until the grains exchange atoms or molecules, and so bond to form a solid mass. (This latter process is called "sintering".) The powder may be mixed with water or other liquid, and allowed to dry before sintering. (This is called "slip forming".) In either case, the nanophase material is allowed to cool in the mold, and the part thus formed is then removed from the mold. If necessary, the part may be further shaped using a diamond-studded burr or other tool.

Figure 2:
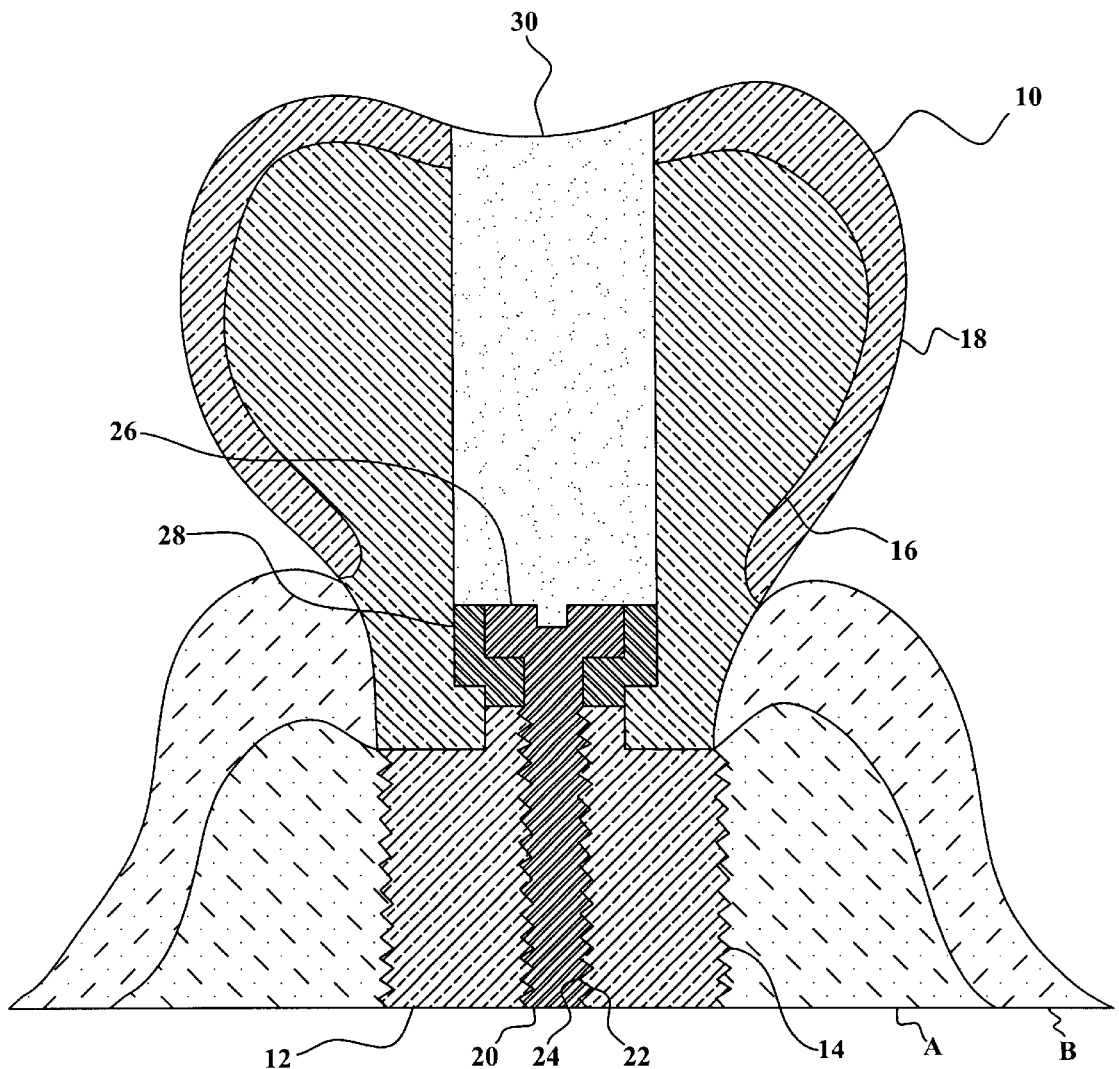
FIG. 2 is a vertical section view of the first preferred embodiment of the invention.

FIG. 2 is a vertical section view of the first preferred embodiment of the invention 10, embedded in bone tissue A and gum tissue B. A dental implant 12 made of a nanophase ceramic material is secured in the bone tissue by growth of the latter against external threads 14. Above the implant rests an abutment 16, also made of nanophase ceramic material, which has a porcelain overcoat 18 for esthetic purposes. The porcelain overcoat is formed by brushing layers of moistened porcelain powder over the external surface of the abutment, allowing it to dry, and then firing it in a kiln. The abutment is retained on the implant by a screw 20, which may be made of nanophase metal, gold alloy, or other suitable material, with screw threads 22 that engage internal threads 24 in the implant. The head of the screw 26 fits against the washer 28 which is mechanically bonded to the abutment, and may be made of nanophase metal, gold alloy, or other suitable material. The screw is inserted through a bore hole in the abutment, which after the screw is inserted and tightened, is filled by resin 30, or alternatively by composite material or other suitable filling.

Figure 3:
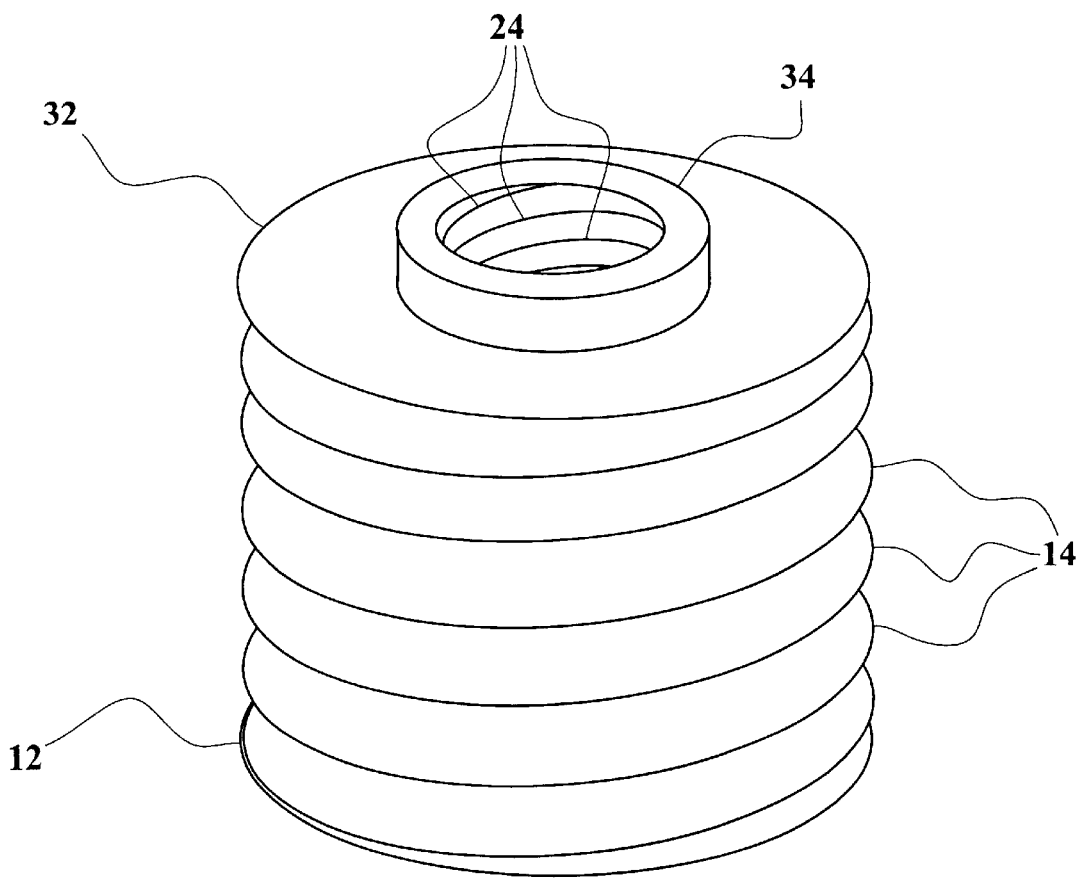
FIG. 3 is a perspective view of the dental implant in the first preferred embodiment of the invention.

FIG. 3 is a perspective view of the dental implant 12 in the first preferred embodiment of the invention, which more clearly shows the external threads 14 and the internal threads 24. From the upper surface 32 of the implant rises an elevated central portion 34, on which the washer rests.

Figure 4:
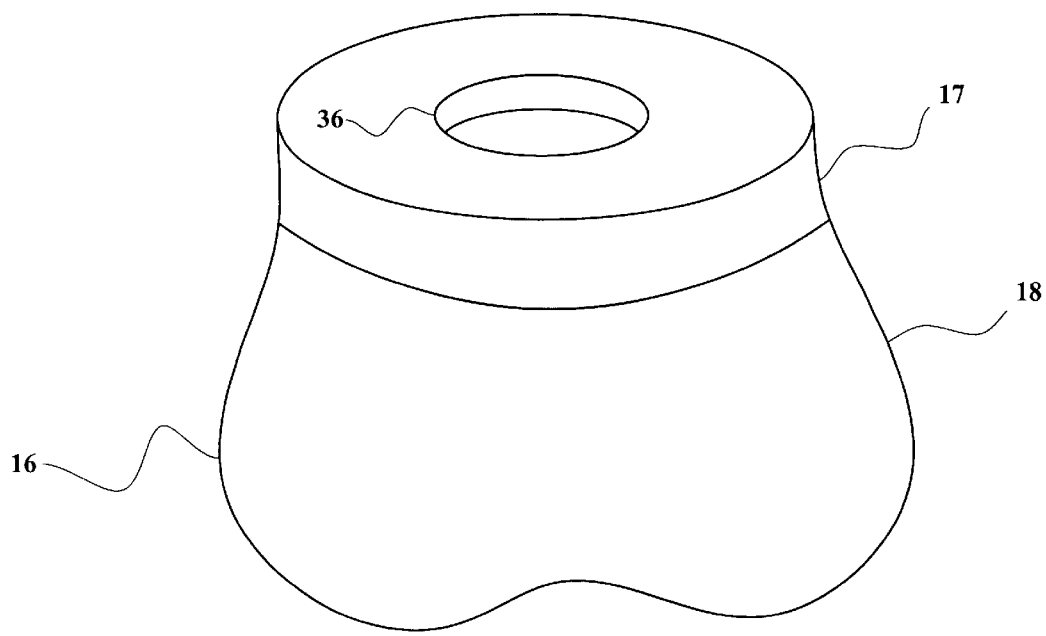
FIG. 4 is a perspective view of the abutment in the first preferred embodiment of the invention.

FIG. 4 is a perspective view of the abutment 16 in the first preferred embodiment of the invention, showing the central bore 36 which is later filled in by a dentist when the prosthetic is inserted. Again, the nanophase material 17 is covered by a porcelain overcoat 18.

Figure 5:
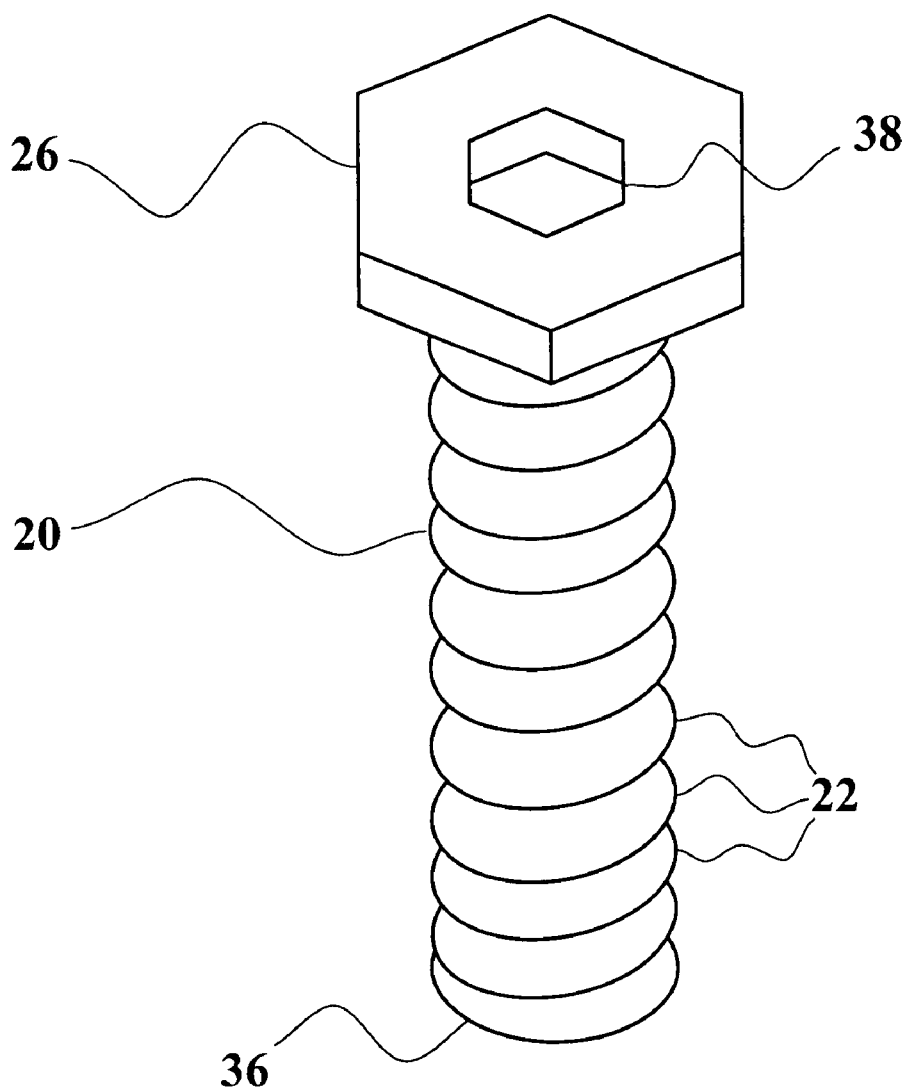
FIG. 5 is a perspective view of the screw in the first preferred embodiment of the invention.

FIG. 5 is a perspective view of the screw 20 in the first preferred embodiment of the invention, more clearly showing the screw threads 22 on the shaft 36 of the screw. The head 26 of the screw is preferably hexagonally shaped, with a hexagonal indentation 38 by which it may be turned by a special hexagonally tipped screw driver.

Figure 6:
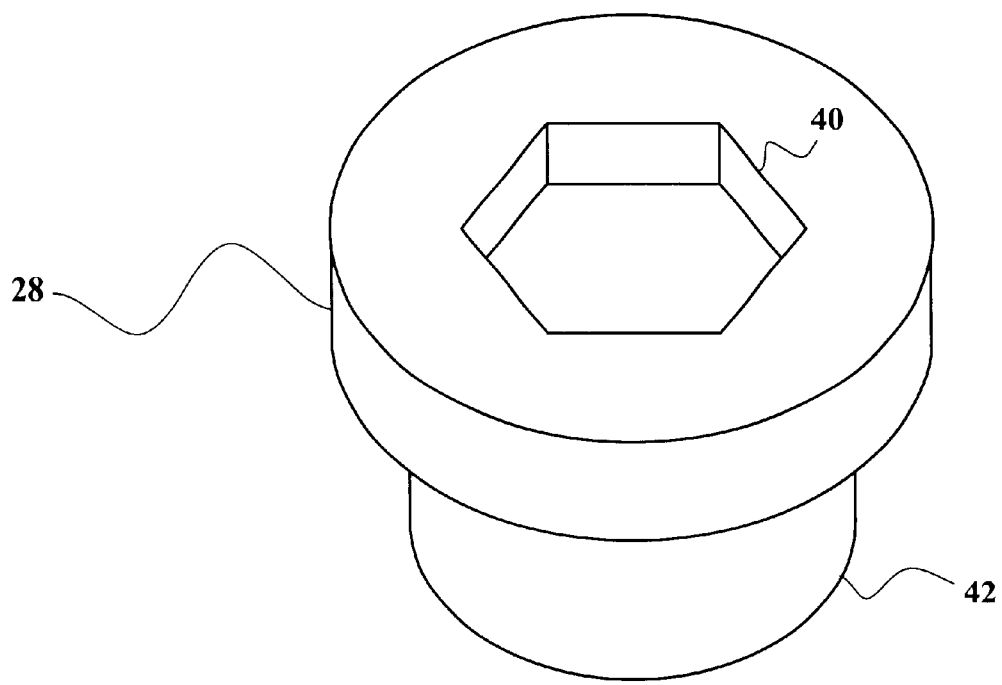
FIG. 6 is a perspective view of the washer in the first preferred embodiment of the invention.

FIG. 6 is a perspective view of the washer 28 in the first preferred embodiment of the invention. The hexagonally shaped opening 40 in the washer engages the hexagonally shaped head of the screw to prevent slippage. The washer has a recessed lower portion 42 to help retain it on the abutment. Preferably, the washer should be inserted into the mold in which the abutment is formed, so that they will become mechanically bonded by virtue of the inevitable unevenness of the washer's surface.

Where two or more adjacent natural teeth have been lost, abutments may be joined together as a "bridge" for added strength (not shown in the drawings).

Figure 7:
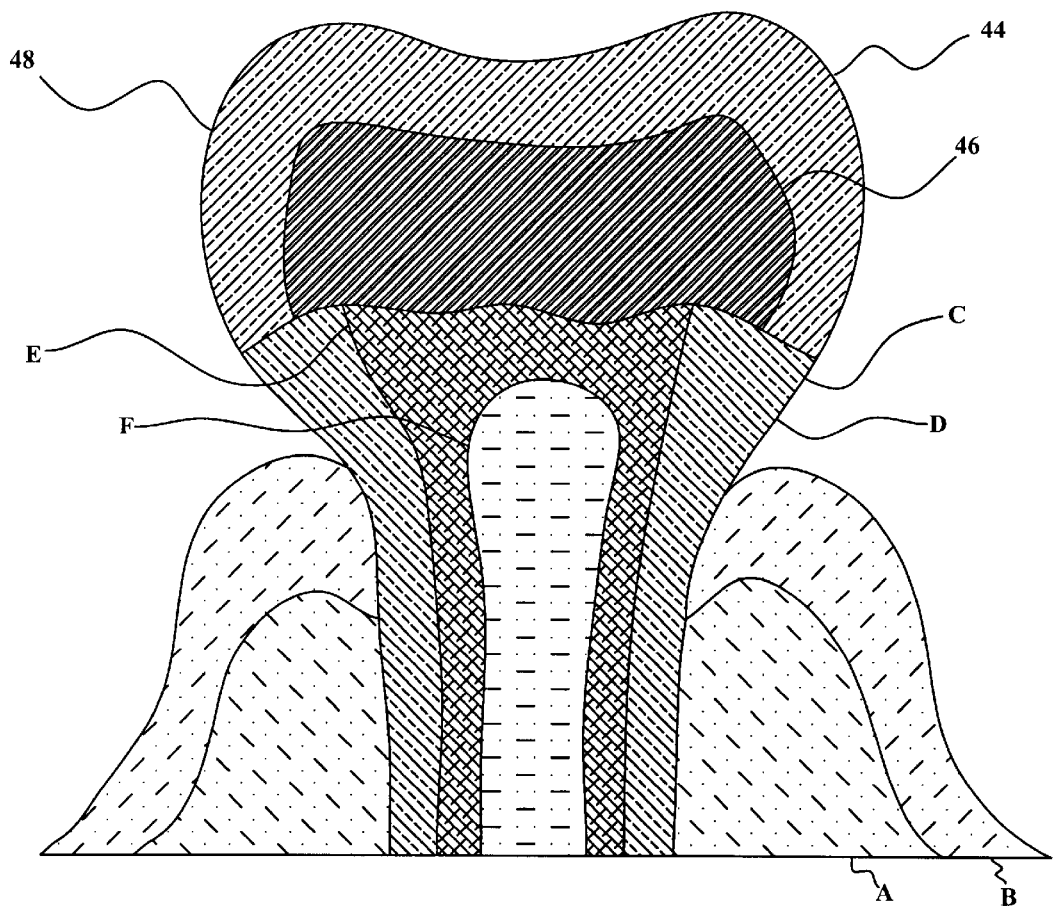
FIG. 7 is a vertical section view of the second preferred embodiment of the invention.

FIG. 7 is a vertical section view of the second preferred embodiment of the invention 44, showing the use of nanophase material in a crown 46 which is covered by a porcelain overcoat 48. The crown is attached to the remaining portion of the tooth C by a cementum (not shown in the drawings). The remaining enamel D, dentin E, and pulp F of the natural tooth are still embedded in the bone tissue A and gum tissue B. Where two or more adjacent teeth require crowns, the crowns may be joined together as a "bridge" for added strength (not shown in the drawings).

When it is necessary to insert an implant into the jaw at an angle, a crown may be place over the abutment (not shown in the drawings). This may be necessary to insure that the prosthetic is properly aligned in the jaw with the natural teeth and/or other artificial teeth.

It is preferable that the nanophase material be biologically inert. The nanophase material may be a biologically inert ceramic, a biologically inert metal, or another biologically inert material or combination of materials.

It is to be understood that the present invention is not limited to the sole embodiment described above, but encompasses any and all embodiments within the scope of the following claims. In particular, it covers any use of any nanophase material in any dental implant, crown, bridge, or other prosthetic.

We claim:

1. A method of making a nanophase dental prosthetic, comprising the steps of:

heating a precursor material to form a vapor;

condensing the vapor by contact with a cold gas to form a nanophase material;

placing the nanophase material in a mold to form a nanophase portion of a dental prosthetic, said dental prosthetic being suitably dimensioned and configured to replace at least part of at least one natural tooth.

2. A method of making a nanophase dental prosthetic according to claim 1, wherein at least one nanophase portion is combined with at least one non-nanophase portion made of a material that is not a nanophase material, to form the dental prosthetic.

3. A method of making a nanophase dental prosthetic according to claim 1, wherein the nanophase material is heated to a liquid state before being placed in the mold, and then is cooled to a solid state in the mold.

4. A method of making a nanophase dental prosthetic according to claim 1, wherein the nanophase material is placed in the mold in a powdered form, and then sintered.

5. A nanophase dental prosthetic, comprising:

a first part made of a metallic nanophase material, and a second part made of a ceramic nanophase material, wherein the metallic and ceramic nanophase materials have grains with a mean diameter of no more than one hundred nanometers.

6. A nanophase dental prosthetic according to claim 5, wherein the nanophase materials have been formed using precursor materials that have been heated to form vapors, and the vapors have been condensed to form said nanophase material.

7. A nanophase dental prosthetic according to claim 6, wherein the vapors have been condensed by contact with cold gas.

8. A nanophase dental prosthetic according to claim 5, wherein the first part and the second part form a replacement for all of at least one natural tooth.

9. A nanophase dental prosthetic according to claim 5, wherein the first part and the second part form a replacement for a portion of at least one natural tooth.

10. A nanophase dental prosthetic according to claim 5, wherein at least one of the nanophase materials has been heated to a liquid state, and then cooled to a solid state in a mold.

11. A nanophase dental prosthetic according to claim 5, wherein at least one of the nanophase materials has been placed in a mold in powdered form, and then sintered.

12. A nanophase dental prosthetic according to claim 5, wherein the nanophase material of the first part and/or the second part are biologically inert.

* * * * *